United States Patent [19]

Buchecker et al.

[11] Patent Number: 4,770,503

[45] Date of Patent: Sep. 13, 1988

[54] LIQUID CRYSTALLINE COMPOUNDS

[75] Inventors: Richard Buchecker, Basel; Martin Schadt, Seltisberg, both of Switzerland

[73] Assignee: Hoffmann-LaRoche Inc., Nutley, N.J.

[21] Appl. No.: 58,663

[22] Filed: May 27, 1987

Related U.S. Application Data

[63] Continuation of Ser. No. 838,068, Mar. 10, 1986, abandoned.

[30] Foreign Application Priority Data

Mar. 26, 1985 [CH] Switzerland ............... 1316/85
Jan. 8, 1986 [CH] Switzerland ................. 32/86

[51] Int. Cl.$^4$ ............... G02F 1/13; C09K 19/34; C09K 19/30; C09D 239/00; C09D 239/02; C07C 161/04

[52] U.S. Cl. ............... 350/350 R; 252/299.5; 252/299.61; 252/299.63; 544/242; 544/335; 558/17; 558/411; 558/425

[58] Field of Search ........... 252/299.66, 299.5, 299.63, 252/299.61, 299.01; 350/350 R; 558/17, 411, 425; 544/242, 335

[56] References Cited

U.S. PATENT DOCUMENTS

| | | | |
|---|---|---|---|
| 3,997,536 | 12/1976 | Boller et al. | 252/299.61 |
| 4,062,798 | 12/1977 | Boller et al. | 252/299.61 |
| 4,130,502 | 12/1978 | Eidenschine et al. | 252/299.63 |
| 4,261,651 | 4/1981 | Gray et al. | 252/299.63 |
| 4,410,445 | 10/1983 | Baur et al. | 252/299.63 |
| 4,490,305 | 12/1984 | Eidenschine et al. | 252/299.63 |
| 4,512,636 | 4/1985 | Andrews et al. | 252/299.61 |
| 4,528,116 | 7/1985 | Dabrowski et al. | 252/299.61 |
| 4,565,425 | 1/1986 | Petrzilka et al. | 252/299.5 |
| 4,621,901 | 11/1986 | Petrzilka et al. | 252/299.63 |
| 4,629,581 | 12/1986 | Boller et al. | 252/299.66 |
| 4,654,421 | 3/1987 | Tanaka et al. | 252/299.63 |
| 4,676,604 | 6/1987 | Petrzilka | 252/299.63 |
| 4,709,030 | 11/1987 | Petrzilka et al. | 252/299.63 |
| 4,719,032 | 1/1988 | Wachtler et al. | 252/299.63 |

FOREIGN PATENT DOCUMENTS

| | | | |
|---|---|---|---|
| 356120 | 4/1980 | Austria | 252/299.61 |
| 0084194 | 7/1983 | European Pat. Off. | 252/299.63 |
| 0122389 | 10/1984 | European Pat. Off. | 252/299.63 |
| 0126883 | 12/1984 | European Pat. Off. | 252/299.63 |
| 168683 | 1/1986 | European Pat. Off. | 252/299.61 |
| 0167912 | 1/1986 | European Pat. Off. | 252/299.63 |
| 0169327 | 1/1986 | European Pat. Off. | 252/299.63 |
| 170082 | 2/1986 | European Pat. Off. | 252/299.61 |
| 172360 | 2/1986 | European Pat. Off. | 252/299.63 |

(List continued on next page.)

OTHER PUBLICATIONS

Schadt, M. et al. Eurodisplay '84, Proceeding of the S.E.E. Fourth Display Conference, Paris, pp. 53–56, Sep. 18–20, 1984.

(List continued on next page.)

Primary Examiner—Teddy S. Gron
Attorney, Agent, or Firm—Jon S. Saxe; Bernard S. Leon; George W. Johnston

[57] ABSTRACT

Compounds of the formula

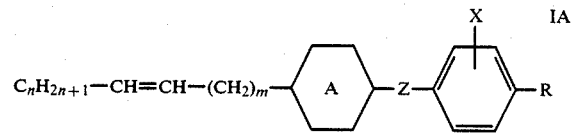

wherein m stands for a whole number of 4–7 and n stands for 0 or a positive whole number; ring A represents trans-1,4-cyclohexylene or a 2,5-disubstituted pyrimidine ring; Z signifies a single covalent bond or, insofar as ring A represents trans-1,4-cyclohexylene, also the ethylene group —CH$_2$CH$_2$—; X denotes hydrogen or fluorine; and R represents the group —NCS or —CN, their manufacture, liquid crystalline mixtures which contain these compounds and the use of these compounds and mixtures for electro-optical purposes are described.

24 Claims, No Drawings

FOREIGN PATENT DOCUMENTS

| | | | |
|---|---|---|---|
| 2636684 | 2/1978 | Fed. Rep. of Germany | 252/299.63 |
| 3315295 | 10/1984 | Fed. Rep. of Germany | 252/299.61 |
| 59-199649 | 11/1984 | Japan | 252/299.67 |
| AP160/1127-23 | 6/1985 | Japan | 252/299.63 |
| 60-146868 | 8/1985 | Japan | 252/299.63 |
| 60-222458 | 11/1985 | Japan | 252/299.63 |
| 61-00289 | 1/1986 | Japan | 252/299.63 |
| 61-27929 | 2/1986 | Japan | 252/299.63 |
| 61-27928 | 2/1986 | Japan | 252/299.63 |
| 61-27931 | 2/1986 | Japan | 252/299.66 |
| 85/04874 | 11/1985 | PCT Int'l. Appl. | 252/299.63 |
| 646725 | 12/1984 | Switzerland | 252/299.63 |
| 2002767 | 2/1979 | United Kingdom | 252/299.66 |
| 2121406 | 12/1983 | United Kingdom | 252/299.63 |

OTHER PUBLICATIONS

Petrzilka, M. et al., Mol. Cryst. Liq. Cryst., vol. 131, pp. 327–342 (Dec. 1985).

Schadt, M. et al., Abstract G52, 10th International Liquid Crystal Conference, United Kingdom, Jul. 15–21, 1984.

Petrzilka, M., Mol. Cryst. Liq. Cryst., vol. 111, pp. 329–346 (1984).

Petrzilka, M., Mol. Cryst. Liq. Cryst., vol. 131, pp. 109–123 (Oct. 1985).

Dabrowski, R. et al., Mol. Cryst. Liq. Cryst., vol. 124, pp. 241–257 (Mar. 1985).

Baran, J. W. et al., Mol. Cryst. Liq. Cryst., vol. 123, pp. 237–245 (1985).

R. Dabrowski, Mol. Cry. Liq. Cry., 87, 109–135 (1982).

M. Schadt, Mol. Cryst. Liq. Cryst., 122, 241–260 (1985).

LIQUID CRYSTALLINE COMPOUNDS

This application is a continuation of application Ser. No. 838,068, filed Mar. 10, 1986, now abandoned.

BACKGROUND OF THE INVENTION

1. Field of the Invention

This invention relates to liquid crystalline compounds and mixtures. More particularly, the present invention is concerned with novel alkenyl-substituted phenylisothiocyanates and benzonitriles as well as liquid crystalline mixtures which contain these compounds and the use of the compounds and mixtures for electro-optical purposes.

2. Description

Liquid crystals have acquired significance primarily as dielectrics in indicating devices, as the optical properties of such substances can be influenced by an electrical voltage. Electro-optical devices based on liquid crystals are known to the person skilled in the art and can be based on various effects such as, for example, the dynamic scattering, the deformation of aligned phases (DAP type), the Schadt-Helfrich effect (rotation cell), the guest/host effect (guest/host cell) or a cholesteric-nematic phase transition (phase change cell).

In order to be suitable as dieletrics for electro-optical indicating devices liquid crystals must, however, satisfy a number of requirements. For example, they must have a good chemical stability with respect to environmental influences such as e.g. heat, moisture, air and electromagnetic radiation in the infrared, visible and ultraviolet range. Further, they should be colourless, should give a good contact and should have a nematic or cholesteric mesophase in the entire temperature range in which the liquid crystal cell is to be operated. Furthermore, the liquid crystals should have low viscosities and short response times. The latter is especially important when they are used in television apparatus. Further, a high multiplexibility and at the same time steep transmission curves are required for indicators with a high density of information. Further properties must fulfill different conditions depending on the type of cell which is used. For example, liquid crystals which are used in rotation cells should have a large positive anisotropy of the dielectric constants ($\Delta\epsilon = \epsilon_{||} - \epsilon_{\perp} > 0$, $\epsilon_{||}$ signifying the dielectric constant along the longitudinal axis of the molecule and $\epsilon_{\perp}$ signifying the dielectric constant perpendicular thereto), and liquid crystals which are used in guest/host cells should have a large positive or negative anisotropy of the dielectric constants. Moreover, in both cases a low threshold potential and a conductivity which is as low as possible are desirable.

As it is generally not possible to achieve all of the desired and to some extent inconsistent properties with a single compound, attempts have mainly been made to optimize the properties for the respective uses by mixing several components. Having regard to the high requirements in the case of uses with a high density of information and especially in the case of uses in television apparatus and autos, there exists, however, a need for further components with which especially the response times and the steepness of the transmission curves can be improved further.

The present invention provides novel liquid crystalline compounds and mixtures possessing such desired properties.

SUMMARY OF THE INVENTION

The present invention is concerned with alkenyl-substituted compounds of the formula

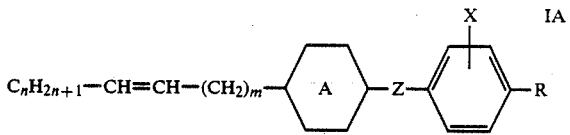

and especially alkenyl-substituted phenylisothiocyanates of the formula

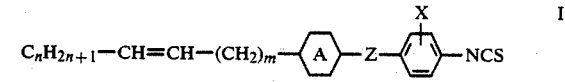

wherein m is an integer of 4 to 7 of and n is zero or a positive integer of up to 20; ring A is trans-1,4-cyclohexylene or a 2,5-disubstituted pyrimidine; Z is a single covalent bond or, when ring A is trans-1,4-cyclohexylene, Z also can be —CH$_2$CH$_2$—; X is hydrogen or fluorine; and R is —NCS or —CN.

When used in electro-optical displays the phenylisothiocyanates (R=NCS) give steep transmission curves, high multiplicity and they enable low voltages to be utilized. In addition to the above properties the benzonitriles (R=CN) also are liquid crystalline intermediates for producing the inventive phenylisothiocyanates.

DETAILED DESCRIPTION OF THE INVENTION

The present invention is concerned with alkenyl-substituted compounds of the formula

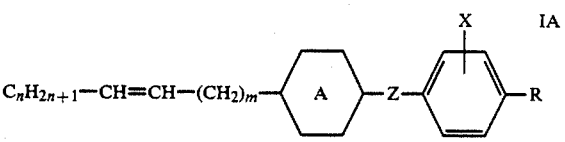

wherein m is an integer of 4 to 7 and n is zero or a positive integer of up to 20; ring A is trans-1,4-cyclohexylene or 2,5-disubstituted pyrimidine; Z is a single covalent bond or, when ring A is trans-1,4-cyclohexylene, Z also can be —CH$_2$CH$_2$—; X is hydrogen or fluorine; and R is —NCS or —CN.

The present invention especially concerns alkenyl-substituted phenylisothiocyanates of the formula

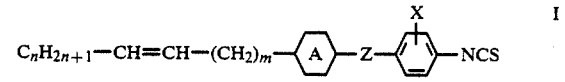

wherein m, n, ring A, Z and X are as described above.

The phenylisothiocyanates in accordance with the invention have, in particular, a favourable ratio of the elastic constants k$_{33}$ (bend) and k$_{11}$ (splay) and when used in electro-optical devices give steep transmission curves and a high multiplexibility. Moreover, they possess a large positive anisotropy of the dielectric constants and enable low operating voltages to be used. Furthermore, the compounds in accordance with the invention have low viscosities and when used in electro-optical devices give very short switching times. The compounds in accordance with the invention are colourless, chemically stable and have a good miscibility with known liquid crystals. The mesophase ranges lie in a temperature range which is favourable for electro-optical uses, in particular the melting points generally lie at relatively low temperatures. The benzonitriles in accordance with the invention (R=CN) are liquid crystalline intermediates in the manufacture of the phenylisothiocyanates and themselves possess comparable properties to the phenylisothiocyanates.

As used herein, "alkyl" denotes straight or branch chained alkyl groups of 1 to 20 carbon atoms, preferably 1 to 6 carbon atoms. Suitable alkyl groups include methyl ethyl, propyl, isopropyl, butyl, pentyl and the like.

Formula IA above embraces isothiocyanates of the following formulae

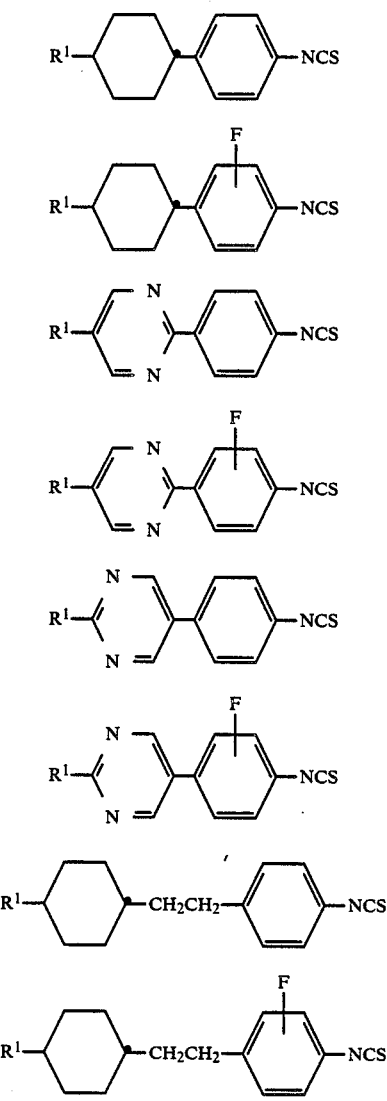

wherein $R^1$ is $C_nH_{2n+1}$—CH=CH—$(CH_2)_m$— and m and n have the above significances,
as well as the benzonitriles corresponding to formulae Ia-Ih which have the group —CN in place of the group —NCS.

In formulae IA and Ia-Ih above m signifies the numbers 4, 5, 6 and 7 and n signifies the numbers 0, 1, 2, 3, 4, 5, 6 etc, preferably up to 10. That is, the group $C_nH_{2n+1}$—CH=CH$(CH_2)_m$— or $R^1$ stands for 5-alkenyl such as 5-hexenyl, 5-heptenyl, 5-octenyl, 5-nonenyl, 5-decenyl, 5-undecenyl and 5-dodecenyl, for 6-alkenyl such as 6-heptenyl, 6-octenyl, 6-nonenyl, 6-decenyl, 6-undecenyl and 6-dodecenyl, for 7-alkenyl such as 7-octenyl, 7-nonenyl, 7-decenyl, 7-undecenyl and 7-dodecenyl, or for 8-alkenyl such as 8-nonenyl, 8-decenyl, 8-undecenyl, 8-dodecenyl and the like. The alkenyl groups can be present in the E or Z-form where n>0. That is, formulae IA, I and Ia-Ih embrace not only pure isomers but also mixtures of isomers.

A lateral fluorine substituent X which may be present is preferably in the ortho-position to the group —NCS or —CN. However, there are especially preferred those compounds in which X signifies hydrogen, i.e. the compounds of formulae Ia, Ic, Ie and Ig, and the corresponding benzonitriles.

In formulae IA and I above Z preferably signifies a single covalent bond. Ring A preferably denotes trans-1,4-cyclohexylene.

The residue $C_nH_{2n+1}$ embraces, besides hydrogen (where n=0), not only straight-chain but also branched alkyl groups. Hydrogen and straight-chain alkyl, i.e. residues of the formula H—$(CH_2)_n$—, are preferred.

Preferred alkenyl substituents in formulae IA, I and Ia-Ih above are those with a maximum of 12 carbon atoms, i.e. the sum m+n preferably amounts to a maximum of 10.

The compounds of formula I can be produced in accordance with the invention by reacting a compound of the formula

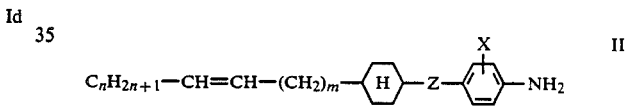

wherein m, n, X, Z and ring A have the above significances.

in the presence of an amine with thiophosgene or in succession with carbon disulphide and a chloroformic acid ester.

The reaction of the compounds of formula II can be carried out in a manner known per se. Preferred amines are dialkylamines and trialkylamines, especially those in which "alkyl" stands in each case for groups with 1 to 7 carbon atoms. Triethylamine is especially preferred. Preferred chloroformic acid esters are the alkyl chloroformates in which the alkyl portion has 1 to 7 carbon atoms, such as methyl chloroformate and ethyl chloroformate. The reaction is conveniently carried out in a polar organic solvent, for example an ether, a chlorinated hydrocarbon or a nitrile such as tetrahydrofuran, dioxan, methylene chloride, chloroform or acetonitrile. The ammonium dithiocarbamate which is obtained in the reaction with carbon disulphide can be isolated if desired or can be further reacted directly with the chloroformic acid ester. However, the reaction with thiophosgene, which leads directly to the desired isothiocyanate, is preferred. Temperature and pressure in the process in accordance with the invention are not critical. However, the reaction is preferably carried out at atmospheric pressure and at a temperature of about 0°–40° C.

The compounds of formula II are novel. They can be prepared, for example, from the corresponding benzonitriles according to the following Reaction Scheme 1 in which m, n, X, Z and ring A have the above significances:

Scheme I

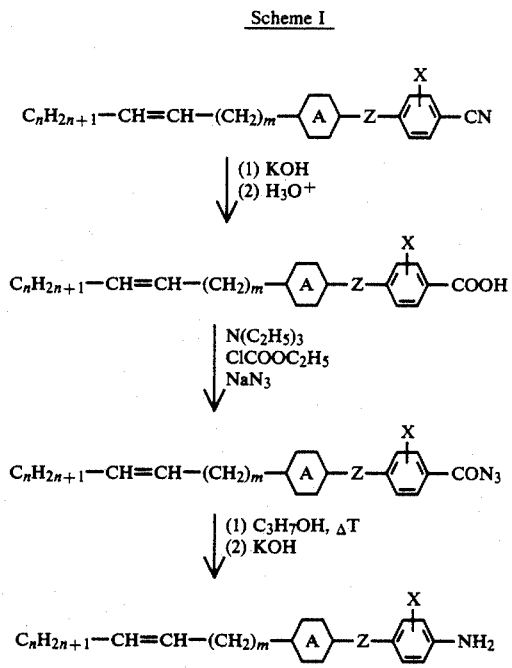

The compounds of formula VII are novel and are also an object of the present invention. They also have liquid crystalline properties, favourable elastic constants, a large positive anisotropy of the dielectric constants and a low viscosity and, when used in electro-optical devices, facilitate low threshold potentials, steep transmission curves and short response times. They can be used in the form of mixtures with one another and/or with other liquid crystal components, especially in admixture with the compounds of formula I and/or the compounds of formulae XX–XXIX set forth below.

The compounds of formula VII can be prepared, for example, on the basis of the following Reaction Schemes 2–4 in which Ts denotes p-tosyl, Z stands for a single covalent bond or the ethylene group —CH$_2$CH$_2$— and m, n and X have the above significances:

Scheme 2

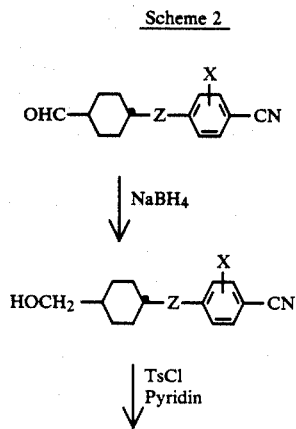

Scheme 2

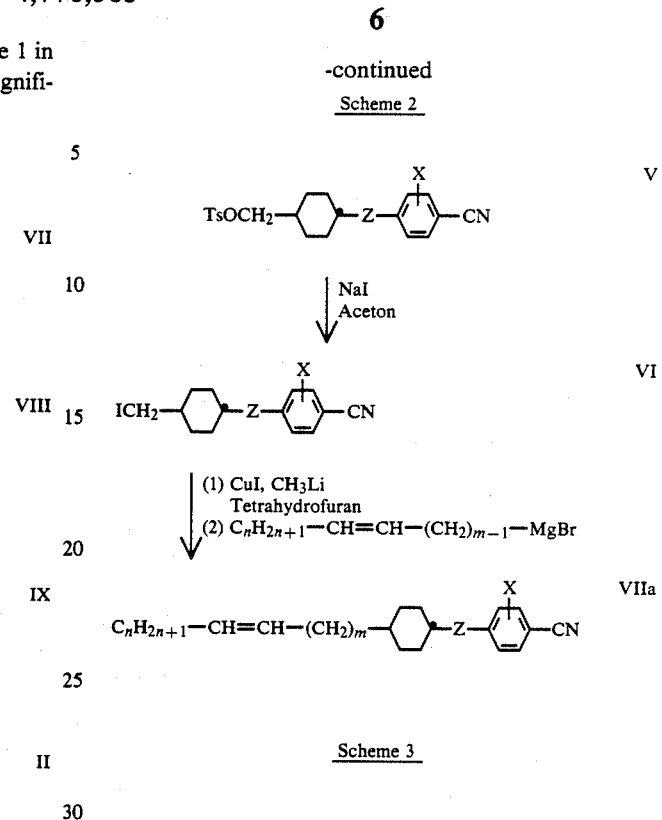

Scheme 3

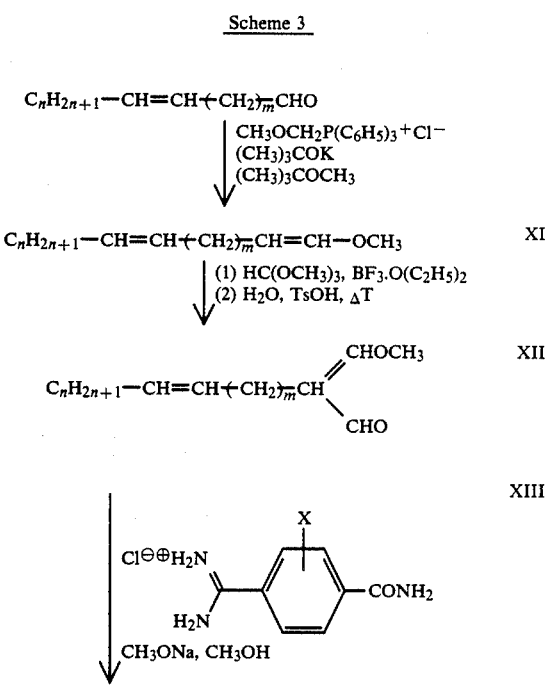

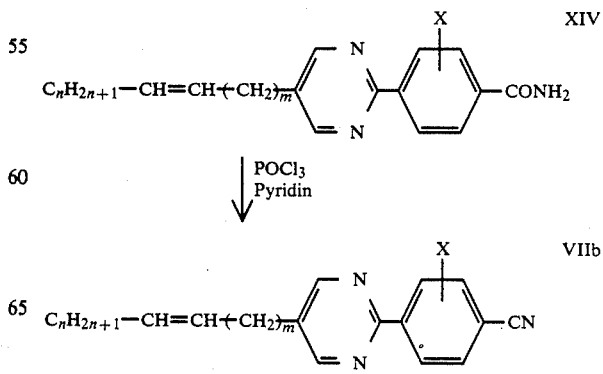

Scheme 4

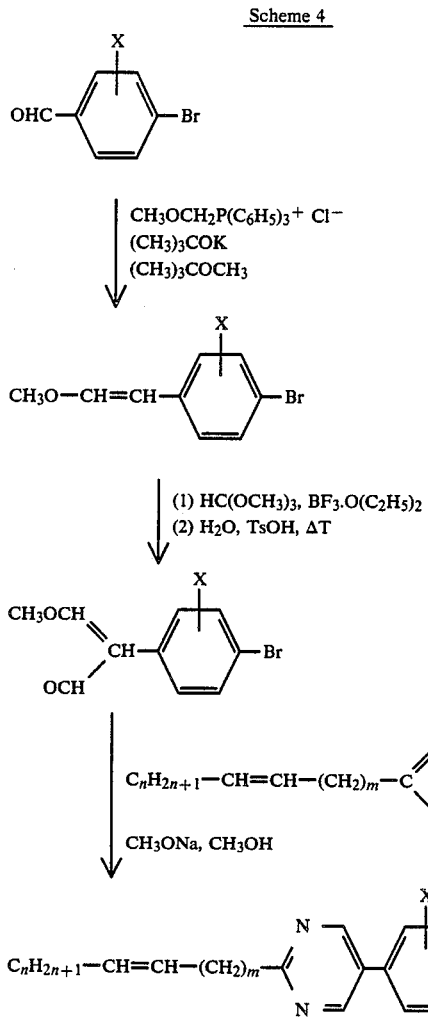

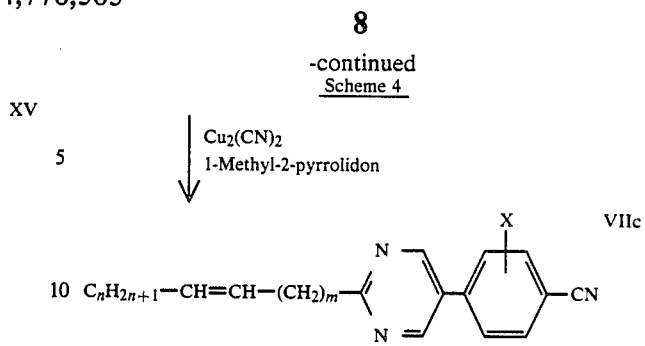

The starting materials which are used in Schemes 2–4 above are known compounds or are analogues of known compounds and can be prepared according to known methods. The compounds of formulae XIII and XVIII can be obtained, for example, from the corresponding nitriles by reaction with hydrochloric acid in methanol and subsequent treatment with ammonia.

The compounds of formula IA can be used in the form of mixtures with one another and/or with usual liquid crystal components, i.e. the mixtures in accordance with the invention contain at least two components with at least one component being a compound of formula IA, preferably a compound of formula I.

Having regard to the favourable properties of the compounds of formula IA and their good miscibility with other liquid crystal components, the amount of the compounds of formula IA in the mixtures in accordance with the invention can vary in wide limits. The mixtures in accordance with the invention preferably contain about 1–60 wt.%, particularly about 5–40 wt.%, of compounds of formula IA or I.

Preferred components which can be used in admixture with one or more compounds of formula IA or I are the compounds of the formulae

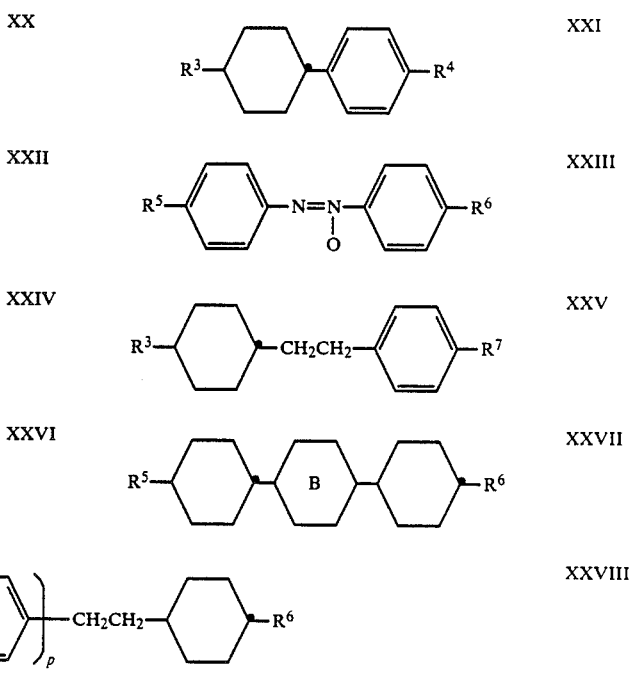

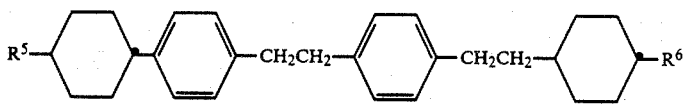

XXIX wherein ring B represents 1,4-phenylene or a 2,5-disubstituted pyrimidine ring; $R^2$ signifies straight-chain alkyl or 3E-alkenyl; $R^3$ denotes straight-chain alkyl, 1E-alkenyl or 3E-alkenyl; $R^4$ stands for cyano, —NCS or straight-chain alkyl or alkoxy; $R^5$ and $R^6$ signify straight-chain alkyl; $R^7$ denotes cyano or straight-chain alkoxy; $R^8$ signifies cyano or straight-chain alkyl; p stands for 0 or 1; and the residues $R^2$–$R^8$ have a maximum of in each case 12, preferably a maximum of in each case 7, carbon atoms.

The mixtures in accordance with the invention can also contain suitable optically active compounds, for example optically active biphenyls, and/or dichroic colouring substances, for example azo, azoxy or anthraquinone colouring substances. The amount of such compounds is determined by the solubility and the desired pitch, colour, extinction and the like. Preferably, the amount of optically active compounds amounts to a maximum of about 4 wt.% and the amount of dichroic colouring substances amounts to a maximum of about 10 wt.%.

The manufacture of the liquid crystalline mixtures in accordance with the invention can be carried out in a manner known per se, e.g. by heating a mixture of the components to a temperature barely above the clearing point and subsequently cooling down.

The manufacture of electro-optical devices which contain a mixture in accordance with the invention as the dielectric can also be carried out in a manner known per se, e.g. by evacuating a suitable cell and introducing the mixture into the evacuated cell.

The manufacture of the compounds of formula IA is illustrated further by the following Examples. C signifies a crystalline phase, S signifies a smectic phase, N signifies a nematic phase and I signifies the isotropic phase. Unless otherwise stated, percentages and ratios relating to solvent mixtures are expressed in volume, purity data determined by gas chromatography are expressed in area % and the remaining percentages and ratios are expressed in weight, temperatures are in degrees Celsius (°C.), normal pressure is about 1 atmosphere and room temperature is about 23° C. The petroleum ether is a well known mixture of low-boiling hydrocarbons. Unless otherwise indicated, the Examples were carried out as written.

EXAMPLE 1

(a) 60 g of trans-4-(p-cyanophenyl)cyclohexanecarboxaldehyde were dissolved in 500 ml of 0.1N methanolic potassium hydroxide solution and the solution was treated portionwise within 1 hour at 0° C. with 3.1 g of sodium borohydride. Thereafter, the reaction mixture was diluted with about 200 ml of water and cautiously adjusted to pH 2–3 in an ice-bath with about 40 ml of 25 percent hydrochloric acid. The mixture was extracted with methylene chloride and the organic phase was dried over magnesium sulphate and concentrated. Crystallization from a mixture of 250 ml of ethyl acetate and 250 ml of petroleum ether gave 45.75 g of trans-4-(p-cyanophenyl)-hydroxymethylcyclohexane (purity 99.6%) as colourless crystals with m.p. 108° C.

(b) A solution of 15 g of trans-4-(p-cyanophenyl)hydroxymethylcyclohexane in 60 ml of pyridine was treated at 0° C. with 22 g of p-tosyl chloride and then stirred at room temperature for 19 hours. Thereafter, the reaction mixture was poured on to ice-water, adjusted to pH 1 with 25 percent hydrochloric acid and extracted with methylene chloride. The organic phases were washed once with saturated sodium hydrogen carbonate solution and twice with water and then dried over magnesium sulphate. After evaporation of the solvent there were obtained 25.58 g of crude trans-4-(p-cyanophenyl)-p-tosyloxymethylcyclohexane as a white, crystalline residue which was used in the next step without additional purification.

(c) 13.4 g of crude trans-4-(p-cyanophenyl)-p-tosyloxymethylcyclohexane were dissolved in 200 ml of acetone and the solution was treated with 8.15 g of sodium iodide. The mixture was boiled at reflux for 30 minutes, then concentrated and the residue was partitioned between water and diethyl ether. After drying the organic phase over magnesium sulphate and evaporation of the solvent there were obtained 12.5 g of yellowish crystals. Chromatographic separation on silica gel with ethyl acetate/petroleum ether (vol. 1:4) and subsequent crystallization from 140 ml of methanol gave 3.7 g of trans-4-(p-cyanophenyl)-iodomethylcyclohexane as colourless crystals of m.p. 127° C.

(d) A mixture of 705 mg of dry copper-(I) iodide and 7 ml of tetrahydrofuran was treated dropwise with 2.5 ml of a 1.5M solution of methyl lithium in hexane at −78° C. while stirring vigorously and then warmed slowly to 0° C. Subsequently, the mixture was again cooled to −78° C. and treated dropwise by means of a syringe with a 4-pentenyl-magnesium bromide solution (prepared from 90 mg of magnesium and 0.44 ml of 5-bromo-1-pentene in 2 ml of tetrahydrofuran). The reaction mixture was warmed gradually until a red-violet suspension had formed and was then held at 5° C. for 20 minutes. Thereafter, the reaction mixture was again cooled to −78° C., treated dropwise with a solution of 600 mg of trans-4-(p-cyanophenyl)-iodomethylcyclohexane in 5 ml of tetrahydrofuran and then warmed slowly to room temperature. The reaction mixture was stirred at room temperature for a further 30 minutes and then treated with saturated ammonium chloride solution and extracted with diethyl ether. The organic phases were dried over magnesium sulphate and concentrated. Chromatographic separation on silica gel with ethyl acetate/petroleum ether (vol. 5:95) and two-fold recrystallization from methanol gave 165 mg of p-[trans-4-(5-hexenyl)cyclohexyl]benzonitrile (purity 99.75%) as colourless crystals of m.p. (C-N) 45.5° C. and cl.p. (N-I) 52.5° C.

The following compounds can be prepared in an analogous manner:
p-[trans-4-(6-Heptenyl)cyclohexyl]benzonitrile; m.p. (C-N) 19.2° C., cl.p. (N-I) 32.3° C.,
p-[trans-4-(7-octenyl)cyclohexyl]benzonitrile; m.p. (C-N) 38.0° C., cl.p. (N-I) 53.2° C., p-[trans-4-(8-nonenyl)cyclohexyl]benzonitrile,
p-[trans-4-(5E- or 5Z-heptenyl)cyclohexyl]benzonitrile,
p-[trans-4-(5E- or 5Z-octenyl)cyclohexyl]benzonitrile,
p-[trans-4-(6E- or 6Z-octenyl)cyclohexyl]benzonitrile,
o-fluoro-p-[trans-4-(5-hexenyl)cyclohexyl]benzonitrile,
o-fluoro-p-[trans-4-(6-heptenyl)cyclohexyl]benzonitrile,
p-[2-(trans-4-(5-hexenyl)cyclohexyl)ethyl]benzonitrile,
p-[2-(trans-4-(6-heptenyl)cyclohexyl)ethyl]benzonitrile,
p-[2-(trans-4-(7-octenyl)cyclohexyl)ethyl]benzonitrile,
p-[2-(trans-4-(5E- or 5Z-heptenyl)cyclohexyl)ethyl]benzonitrile,
o-fluoro-p-[2-(trans-4-(5-hexenyl)cyclohexyl)ethyl]benzonitrile.

EXAMPLE 2

(a) A mixture of 2.61 g of p-[trans-4-(5-hexenyl)cyclohexyl]benzonitrile and 20 g of potassium hydroxide in 200 ml of diethylene glycol was boiled at 180° C. for 1 hour while gassing with argon in a round flask equipped with a magnetic stirrer and a reflux condenser. After cooling the brown reaction mixture was made acid with 35 ml of 36 percent hydrochloric acid and partitioned between 100 ml of methylene chloride and 100 ml of water. The aqueous phase was back-extracted three times with 100 ml of methylene chloride each time. The organic phases were washed twice with 100 ml of water each time and dried over magnesium sulphate and active charcoal. After separating the solvent in a rotary evaporator there were obtained 2.93 g (104%) of p-[trans-4-(5-hexenyl)cyclohexyl]benzoic acid as brownish, not quite pure crystals; Rf value 0.38 (ethyl acetate/petroleum ether vol. 3:7).

(b) A suspension of 2.8 g of p-[trans-4-(5-hexenyl)cyclohexyl]benzoic acid in 50 ml of acetone and 7 ml of water was cooled to 0° C. and treated slowly with a solution of 2.73 ml of triethylamine in 15 ml of acetone, whereby a clear solution formed. The mixture was subsequently treated dropwise with a solution of 2.33 ml of ethyl chloroformate in 10 ml of acetone, whereby a white flocculent precipitate separated. The mixture was stirred at 0° C. for a further 30 minutes, then treated dropwise with a solution of 1.74 g of sodium azide in 7 ml of water and stirred at 0° C. for a further 1 hour. Thereafter, the reaction mixture was partitioned between 150 ml of methylene chloride and 150 ml of water. The aqueous phase was back-extracted three times with 150 ml of diethyl ether each time. The organic phases were washed twice with 100 ml of water each time and dried over magnesium sulphate. After separating the solvent on a rotary evaporator there were obtained 3.1 g (100%) of p-[trans-4-(5-hexenyl)cyclohexyl]benzoic acid azide as a solid crystalline mass which was further processed in the crude state; Rf value 0.63 (ethyl acetate/petroleum ether vol. 1:9).

(c) A mixture of 3.1 g of crude p-[trans-4-(5-hexenyl)cyclohexyl]benzoic acid azide and 100 ml of propanol was boiled at reflux for 1 hour while gassing with argon and thereafter evaporated. There were thus obtained 3.33 g (97%) of propyl p-[trans-4-(5-hexenyl)cyclohexyl]phenylcarbamate as a pale brown, solid mass which was further processed in the crude state; Rf value 0.39 (ethyl acetate/petroleum ether vol. 1:9).

(d) A mixture of 3.33 g of crude propyl p-[trans-4-(5-hexenyl)cyclohexyl]phenylcarbamate and 150 ml of a 10 percent solution of potassium hydroxide in diethylene glycol/water (vol. 4:1) was boiled at 120° C. for 2 hours, then cooled to room temperature and partitioned between 150 ml of methylene chloride and 150 ml of water. The aqueous phase was back-extracted twice with 150 ml of methylene chloride each time. The organic phases were washed twice with 100 ml of water each time, dried over magnesium sulphate and concentrated. Low-pressure chromatography (0.5 bar) of the brown, crystalline residue (3 g) on 70 g of silica gel with ethyl acetate/petroleum ether (vol. 20:80) gave 2.18 g (88%) of p-[trans-4-(5-hexenyl)cyclohexyl]aniline as light yellowish crystals (purity 98.1%); Rf value 0.20 (ethyl acetate/petroleum ether vol. 1:5).

(e) A solution of 2.36 ml of triethylamine in 15 ml of chloroform was treated dropwise at −10° C. with a solution of 2.18 g of p-[trans-4-(5-hexenyl)cyclohexyl]aniline in 20 ml of chloroform. After 5 minutes the mixture was treated with a solution of 690 μl of thiophosgene in 10 ml of chloroform, warmed to room temperature and stirred for 2 hours. Thereafter, the reaction mixture was partitioned between water and chloroform. The organic phase was dried over magnesium sulphate and concentrated. Chromatographic separation on 140 g of silica gel using ethyl acetate/petroleum ether (vol. 5:95) and subsequent crystallization from 80 ml of methanol and low temperature filtration gave 1.24 g of p-[trans-4-(5-hexenyl)cyclohexyl]phenylisothiocyanate (purity 100%) as a milky liquid of m.p. (C-N) 15.2° C. and cl.p. (N-I) 46.1° C.

At 22° C. p-[trans-4-(5-hexenyl)cyclohexyl]phenylisothiocyanate has a bulk viscosity $\eta$ of 12.1 cP, an optical anisotropy $\Delta n$ of 0.180 and a switching time $t_{off}$ of 26 ms in a rotation cell having an electrode spacing of 8 μm. It is therefore less viscous and enables substantially shorter switching times than the corresponding hexyl derivative. The corresponding values for p-(trans-4-hexylcyclohexyl)phenylisothiocyanate are: $\eta=16.0$ cP, $\Delta n=0.153$, $t_{off}=41$ ms.

The following compounds can be manufactured in an analogous manner:

p-[trans-4-(6-Heptenyl)cyclohexyl]phenylisothiocyanate; m.p. (C-N) 1.6° C., cl.p. (N-I) 19.0° C.,
p-[trans-4-(7-octenyl)cyclohexyl]phenylisothiocyanate; m.p. (C-N) 24.6° C., cl.p. (N-I) 45.4° C.,
p-[trans-4-(8-nonenyl)cyclohexyl]phenylisothiocyanate,
p-[trans-4-(5E- or 5Z-heptenyl)cyclohexyl]phenylisothiocyanate,
p-[trans-4-(5E- or 5Z-octenyl)cyclohexyl]phenylisothiocyanate,
p-[trans-4-(6E- or 6Z-octenyl)cyclohexyl]phenylisothiocyanate,
o-fluoro-p-[trans-4-(5-hexenyl)cyclohexyl]phenylisothiocyanate,
o-fluoro-p-[trans-4-(6-heptenyl)cyclohexyl]phenylisothiocyanate,
p-[2-(trans-4-(5-hexenyl)cyclohexyl)ethyl]phenylisothiocyanate,
p-[2-(trans-4-(6-heptenyl)cyclohexyl)ethyl]phenylisothiocyanate,
p-[2-(trans-4-(7-octenyl)cyclohexyl)ethyl]phenylisothiocyanate,
p-[2-(trans-4-(5E- or 5Z-heptenyl)cyclohexyl)ethyl]phenylisothiocyanate,
p-fluoro-p-[2-(trans-4-(5-hexenyl)cyclohexyl)ethyl]phenylisothiocyanate,
p-[5-(5-hexenyl)-2-pyrimidinyl]phenylisothiocyanate,
p-[5-(6-heptenyl)-2-pyrimidinyl]phenylisothiocyanate,
p-[5-(7-octenyl)-2-pyrimidinyl]phenylisothiocyanate,
p-[5-(8-nonenyl)-2-pyrimidinyl]phenylisothiocyanate, p-[5-(5E- or 5Z-heptenyl)-2-pyrimidinyl]phenylisothiocyanate,
p-[5-(5E- or 5Z-octenyl)-2-pyrimidinyl]phenylisothiocyanate,
p-fluoro-p-[5-(5-hexenyl)-2-pyrimidinyl]phenylisothiocyanate.

EXAMPLE 3

(a) A suspension of 22.3 g of methoxymethyl-triphenylphosphonium chloride in 60 ml of diethyl ether is treated with 7.62 g of potassium t-butylate while stirring. 45 minutes later the mixture is treated with a solution of 3.16 g of 6-heptenal in 30 ml of diethyl ether. After 2 hour at room temperature the mixture is poured on to ice-water. The organic phase is separated, washed with water and dried and the crude 1,7-octadienyl methyl ether obtained is distilled.

(b) A solution of 1.31 g of boron trifluoride etherate in 50 ml of distilled methyl orthoformate is treated dropwise with 2.58 g of 1,7-octadienyl methyl ether while cooling with an ice-bath. The reaction mixture is stirred at room temperature overnight and then diluted with 100 ml of toluene, washed with sodium hydrogen carbonate solution and water and dried. After evaporating the solvent there is obtained crude (5-hexenyl)malon-tetraacetal.

(c) A mixture of 3.77 g of crude (5-hexenyl)malon-tetraacetal, 0.35 ml of water and 15 mg of p-toluene-sulphonic acid is heated to 80°–85° C. for 3 hours while stirring. After cooling the mixture is treated with 160 mg of sodium hydrogen carbonate and stirred for 1.5 hours. Subsequently, the reaction mixture is diluted with diethyl ether, extracted three times with cold 3N sodium hydroxide solution, washed with water and dried. The crude 3-methoxy-2-(5-hexenyl)acrolein which is obtained after evaporation of the solvent is further processed without additional purification.

(d) A solution of 480 mg of sodium in 17.5 ml of methanol is treated with 1.18 g of 3-methoxy-2-(5-hexenyl)acrolein and 1.62 g of 4-amidinobenzamide hydrochloride and the mixture is stirred at 50° C. overnight under nitrogen. After cooling the suspension is treated with 5.5 ml of 3N hydrochloric acid, filtered and the residue is washed with water and dried. The crude p-[5-(5-hexenyl)-2-pyrimidinyl]benzamide obtained is further processed without additional purification.

(e) A suspension of 1.37 g of crude p-[5-(5-hexenyl)-2-pyrimidinyl]benzamide in 15 ml of pyridine is treated with 0.95 ml of benzenesulphonyl chloride and the mixture is heated to 55° C. for 6 hours. Subsequently, the reaction mixture is poured into cold dilute hydrochloric acid and extracted with methylene chloride. The organic phase is washed in succession with hydrochloric acid, sodium hydrogen carbonate solution and water and then dried. After evaporation of the solvent the crude p-[5-(5-hexenyl)-2-pyrimidinyl]benzonitrile is purified by chromatography on silica gel with toluene/acetone and recrystallized.

If desired, the p-[5-(5-hexenyl)-2-pyrimidinyl]benzamide can be hydrolyzed directly in an analogous manner to Example 2a to give p-[5-(5-hexenyl)-2-pyrimidinyl]benzoic acid.

The following compounds can be prepared in an analogous manner:
p-[5-(6-Heptenyl)-2-pyrimidinyl]benzonitrile,
p-[5-(7-octenyl)-2-pyrimidinyl]benzonitrile,
p-[5-(8-nonenyl)-2-pyrimidinyl]benzonitrile,
p-[5-(5E- or 5Z-heptenyl)-2-pyrimidinyl]benzonitrile,
p-[5-(5E- or 5Z-octenyl)-2-pyrimidinyl]benzonitrile,
o-fluoro-p-[5-(5-hexenyl)-2-pyrimidinyl]benzonitrile.

We claim:

1. A compound of the formula

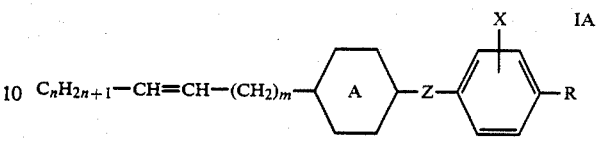

wherein m is an integer of 4 to 7 and n is 0 or a positive integer of up to 20; ring A is trans-1,4-cyclohexylene or 2,5-disubstituted pyrimidine; Z is a single covalent bond or, when ring A is trans-1,4-cyclohexylene, Z also can be —CH$_2$CH$_2$—; X is hydrogen or fluorine; and R is —NCS or —CN.

2. The compound of claim 1, wherein R is —NCS.

3. The compound of claim 1, wherein Z is a single covalent bond.

4. The compound of claim 2, wherein Z is a single covalent bond.

5. The compound of claim 1, wherein ring A is trans-1,4-cyclohexylene.

6. The compound of claim 1, having the formula

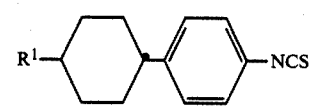

wherein R$^1$ is C$_n$H$_{2n+1}$—CH=CH—(CH$_2$)$_m$— and m is an integer of 4 to 7 and n is 0 or a positive integer of up to 20.

7. The compound of claim 1, wherein the sum of m+n is a maximum of 10.

8. The compound of claim 6, wherein the sum of m+n is a maximum of 10.

9. The compound of claim 1, wherein the residue C$_n$H$_{2n+1}$ is hydrogen or straight-chain alkyl.

10. The compound of claim 6, wherein the residue C$_n$H$_{2n+1}$ of R$^1$ is hydrogen or straight-chain alkyl.

11. The compound of claim 8, wherein the residue C$_n$H$_{2n+1}$ of R$^1$ is hydrogen or straight-chain alkyl.

12. The compound of claim 1, wherein m is the integer 4.

13. The compound of claim 6, wherein m is the integer 4.

14. The compound of claim 1, wherein X is hydrogen.

15. The compound of claim 1, having the formula

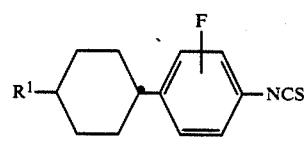

wherein R$^1$ is C$_n$H$_{2n+1}$—CH=CH—(CH$_2$)$_m$— and m is an integer of 4 to 7 and n is 0 or a positive integer of up to 20.

16. The compound of claim 1, having the formula

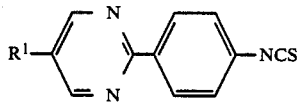

wherein $R^1$ is $C_nH_{2n+1}$—CH=CH—$(CH_2)_m$— and m is an integer of 4 to 7 and n is 0 or a positive integer of up to 20.

17. The compound of claim 1, having the formula

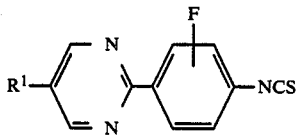

wherein $R^1$ is $C_nH_{2n+1}$—CH=CH—$(CH_2)_m$— and m is an integer of 4 to 7 and n is 0 or a positive integer of up to 20.

18. The compound of claim 1, having the formula

wherein $R^1$ is $C_nH_{2n+1}$—CH=CH—$(CH_2)_m$— and m is an integer of 4 to 7 and n is 0 or a positive integer of up to 20.

19. The compound of claim 1, having the formula

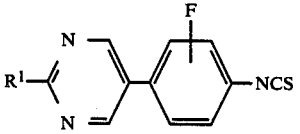

wherein $R^1$ is $C_nH_{2n+1}$—CH=CH—$(CH_2)_m$— and m is an integer of 4 to 7 and n is 0 or a positive integer of up to 20.

20. The compound of claim 1, having the formula

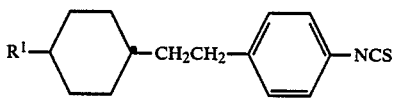

wherein $R^1$ is $C_nH_{2n+1}$—CH=CH—$(CH_2)_m$— and m is an integer of 4 to 7 and n is 0 or a positive integer of up to 20.

21. The compound of claim 1, having the formula

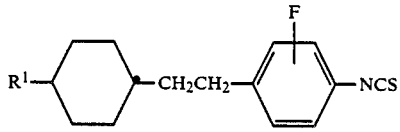

wherein $R^1$ is $C_nH_{2n+1}$—CH=CH—$(CH_2)_m$— and m is an integer of 4 to 7 and n is 0 or a positive integer of up to 20.

22. A liquid crystalline mixture comprising at least two components, wherein at least one of the components is a compound of the formula

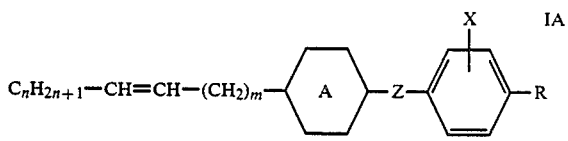

wherein m is an integer of 4 to 7 and n is 0 or a positive integer of up to 20; ring A is trans-1,4-cyclohexylene or 2,5-disubstituted pyrimidine; Z is a single covalent bond or, when ring A is trans-1,4-cyclohexylene, Z also can be —CH$_2$CH$_2$—; X is hydrogen or fluorine; and R is —NCS or —CN.

23. An electro-optical cell comprising:
(a) two plate means;
(b) liquid crystal means disposed between the two plate means and including a compound of the formula

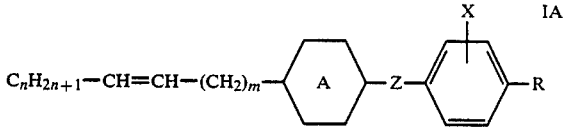

wherein m is an integer of 4 to 7 and n is 0 or a positive integer of up to 20; ring A is trans-1,4-cyclohexylene or 2,5-disubstituted pyrimidine; Z is a single covalent bond or, when ring A is trans-1,4-cyclohexylene, Z also can be —CH$_2$CH$_2$—; X is hydrogen or fluorine; and R is —NCS or —CN; and
(c) means for applying an electrical potential to said plate means.

24. The compound of claim 6, p-[trans-4-(5-hexenyl)-cyclohexyl]phenylisothiocyanate.

* * * * *